(12) United States Patent
Weitzel (10) Patent No.: US 6,167,765 B1
(45) Date of Patent: Jan. 2, 2001

(54) SYSTEM AND METHOD FOR DETERMINING THE FLOW RATE OF BLOOD IN A VESSEL USING DOPPLER FREQUENCY SIGNALS

(75) Inventor: William F. Weitzel, Ypsilanti, MI (US)

(73) Assignee: The Regents of the University of Michigan, Ann Arbor, MI (US)

(*) Notice: Under 35 U.S.C. 154(b), the term of this patent shall be extended for 0 days.

(21) Appl. No.: 09/160,685

(22) Filed: Sep. 25, 1998

(51) Int. Cl.$^7$ ..................................................... G01F 1/20

(52) U.S. Cl. ....................................... 73/861.18; 600/454
(58) Field of Search ........................... 73/861.12, 861.18, 73/861.25, 861.26, 861.27, 861.28, 861.29, 861.31, 861.08, 861; 600/16, 454, 455, 456, 504, DIG. 13

(56) References Cited

U.S. PATENT DOCUMENTS

| | | | |
|---|---|---|---|
| 4,434,669 | * 3/1984 | Roberts et al. | 73/861.25 |
| 4,663,977 | * 5/1987 | Vander Heyden | 73/861.27 |
| 4,820,260 | * 4/1989 | Hayden | 604/4 |
| 4,895,557 | * 1/1990 | Moise et al. | 600/16 |
| 4,913,159 | * 4/1990 | Gardin et al. | 73/861.25 |
| 4,969,865 | * 11/1990 | Hwang et al. | 600/16 |
| 5,078,148 | * 1/1992 | Nassi et al. | 73/861.25 |
| 5,092,836 | 3/1992 | Polaschegg . | |
| 5,312,550 | 5/1994 | Hester . | |
| 5,376,114 | * 12/1994 | Jarvik | 600/16 |
| 5,510,716 | 4/1996 | Buffaloe, IV et al. . | |
| 5,644,240 | 7/1997 | Brugger . | |
| 5,685,989 | 11/1997 | Krivitski et al. . | |
| 5,690,115 | 11/1997 | Feldman et al. . | |

OTHER PUBLICATIONS

C. Langescheid, et al., Anastomosis–Pressure–Dynamic Method for Determining AV Fistual Flood Flow Rate, Dialysis & Transplantation, Jun. 1977, pp. 54–55.

Steve J. Schwab, et al., Prevention of Hemodialysis Fistula Thrombosis. Early Detection of Venous Stenoses, Kidney International, vol. 36 (1989), pp. 707–711.

Anatole Besarab, et al., Utility of Intra–Access Pressure Monitoring in Detecting and Correcting Venous Outlet Stenoses Prior to Thrombosis, Kidney International, vol. 47 (1995), pp. 1364–1373.

Nikolai M. Krivitski, Theory and Validation of Access Flow Measurement by Dilution Technique During Hemodialysis, Kidney International, vol. 48 (1995), pp. 244–250.

(List continued on next page.)

*Primary Examiner*—Max Noori
*Assistant Examiner*—Jagdish Patel
(74) *Attorney, Agent, or Firm*—Brooks & Kushman P.C.

(57) ABSTRACT

A system and method are provided for determining the flow rate of blood in a vessel, such as a hemodialysis access. The system includes a conduit, such as an external dialysis circuit or an intravascular catheter, in communication with the blood in the vessel and having a diversion point for diverting the blood from the vessel into the conduit. As such, the vessel has a flow rate ($Q_A$) upstream from the diversion point and a flow rate ($Q_D$) downstream from the diversion point. A pump is connected to the conduit for diverting the blood into the conduit using a pump flow rate. An ultrasonic sensor is provided in communication with the blood in the vessel downstream from the diversion point. The ultrasonic sensor senses the downstream flow rate ($Q_D$) and generates at least two downstream Doppler frequency signals including a first downstream Doppler frequency signal when the pump has a first pump flow rate and a second downstream Doppler frequency signal when the pump has a second pump flow rate. A processor connected to the ultrasonic sensor and the pump then determines the upstream flow rate ($Q_A$) when the pump has a selected pump flow rate from the first and second downstream Doppler frequency signals and the selected pump flow rate.

25 Claims, 5 Drawing Sheets

OTHER PUBLICATIONS

Richard E. May, et al., Predictive Measures of Vascular Access Thrombosis: A Prospective Study, Kidney International, vol. 52 (1997), pp. 1656–1662.

Barry S. Strauch, et al., Forecasting Thrombosis of Vascular Access with Doppler Color Flow Imaging, American Journal of Kidney Diseases, vol. XIX, No. 6 (Jun.), 1992, pp. 554–557.

Barry Kirschbaum, et al., Study of Vascular Access Blood Flow by Angiodynography, American Journal of Kidney Diseases, vol. 25, No. 1 (Jan.), 1995; pp. 22–25.

David E. Finlay, et al., Duplex and Color Doppler Sonography of Hemodialysis Arteriovenous Fistulas and Grafts, RadioGraphics, vol. 13, No. 5, Sep., 1993 pp. 983–999.

Peter J. Bosman, et al., Access Flow Measurements in Hemodialysis Patients; In Vivo Validation of an Ultrasdound Dilution Technique, Journal of American Society of Neprology, vol. 7, No. 6, 1996, pp. 966–969.

R. M. Lindsay, et al., A Comparison of Methods for the Measurement of Hemodialysis Access Recirculation and Access Blood Flow Rate, ASAIO Journal 1998, pp. 62–67.

C.P. Oates, et al., The Use of a Diasonics DRF400 Duplex Ultrasound Scanner to Measure Volume Flow in Arterio–Venous Fistulae in Patients Undergoing Haemodialysis: An Analysis of Measurement Uncertainties, Ultrasound in Medicine and Biology, vol. 16, No. 6, 1990, pp. 571–579.

Jeffrey Sands, et al., The Effect of Doppler Flow Screening Studies and Elective Revisions on Dialysis Access Failure, ASAIO Journal 1992, pp. M524–M527.

Nikolai M. Krivitski, et al., Development of a Method for Measuring Hemodialysis Access Flow: From Idea to Robust Technology, Seminars in Dialysis, Mar.–Apr. 1998, vol. 11, No. 2, pp. 124–130.

Erjun Wang et al., Predictive Value of Access Blood Flow in Detecting Access Thrombosis, ASAIO Journal 1998, pp. M555–558.

Anatole Besarab et al., The Relationship of Recirculation to Access Blood Flow, American Journal of Kidney Diseases, vol. 29, No. 2 (Feb.), 1997, pp. 223–229.

Kevin L. Sullivan et al., Hemodynamics of Failing Dialysis Grafts, Radiology, Mar. 1993, pp. 867–872.

Marla Paun et al., New Ultrasound Approaches to Dialysis Access Monitoring, American Journal of Kidney Diseases, vol. 35, No. 3 (Mar.), 2000, pp. 477–481 (Manuscript received from Dr. Ulrich Herken on Apr. 28, 1999).

Thomas A. Depner, In–Line Methods, Hemodialysis Access, 1998, pp. 38–39.

Anatole Besarab, et al., The Prevention of Access Failure Pressure Monitoring, Hemodialysis Access, 1998, pp. 35–37.

Jeffrey Sands, et al., Hemodialysis Access Flow Measurement Comparision of Ultrasound Dilution and Duplex Ultrasonography, ASAIO Journal, 1996, pp. M899–M901.

Jeffrey Sands, The Role of Color–Flow Doppler Ultrasound in the Management of Hemodialysis Accesses, ASAIO Journal, 1998, pp. 41–43.

Thomas A. Depner et al., Pressure Effects on Roller Pump Blood Flow During Hemodialysis, ASAIO Journal , 1990, pp. M456–M459.

* cited by examiner

SYSTEM AND METHOD FOR DETERMINING THE FLOW RATE OF BLOOD IN A VESSEL USING DOPPLER FREQUENCY SIGNALS

TECHNICAL FIELD

This invention relates to the field of hemodynamics, and more particularly to a system and method for measuring blood flow rate in a vessel, such as a hemodialysis access.

BACKGROUND ART

Hemodialysis is a process by which blood is passed through an external dialysis circuit to replace the function of a patient's kidney. Blood is removed from the patient's vascular system via an arterial line, is passed through a dialysis filter, and is returned to the patient via a venous line. In order to simplify the withdrawal and return of blood, many dialysis patients have an arteriovenous shunt, or access, surgically created between an artery and vein in a location in the body, such as the upper or lower arm. The access provides a permanent site where the arterial line and venous line can be connected to the patient. A vascular access may be constructed from a native arteriovenous fistula, which is a direct connection of a patient's artery to one of his/her veins, or alternatively may be constructed from a synthetic material, typically polytetrafluoroethylene (PTFE).

While a permanent vascular access provides a convenient connection site for arterial and venous lines, malfunction of such an access is a frequent occurrence in patients receiving chronic hemodialysis. Specifically, unpredictable thrombosis and stenosis in an access causes a reduction in blood flow which necessitates correction through angioplasty or other surgical means. If untreated, low blood flow can cause undesired recirculation in the access, where some part of the freshly dialyzed blood from the venous line flows upstream to the arterial line where it is again filtered. Studies have shown that decreased hemodialysis access flow is associated with an increased risk of access thrombosis and stenosis, such that early detection of an access with a low flow rate is essential in order to prevent more serious complications (see May et al., *Kidney Int.* 52: 1656–1662, 1997).

Therefore, the importance of sufficient access flood flow has resulted in the emergence of access surveillance as a necessary component in the care of patients on hemodialysis. Surveillance techniques have been developed to detect low blood flow predictive of future thrombosis and stenosis.

An early method of calculating the access flow rate involves occluding the access, placing a needle into the access to monitor the pressure therein, and pumping blood around the occlusion to determine the relationship between blood flow rate and pressure within the access. This intra-access pressure monitoring may be performed either upstream (see Langescheid et al., *Dialysis and Transplantation* June: 54–55, 1977) or downstream (see Brosman et al., *J. Am. Soc. Nephrol.* 7: 966–969, 1996) from the occlusion. Unfortunately, occlusion of the access may lead to thrombosis, and placement of the needle or pressure sensor within the access is invasive. Static and dynamic venous pressure monitoring, whereby the pressure within the access is measured with the dialysis blood pump off (static) or on (dynamic), have also been used for surveillance (see Besarab et al., *ASAIO J.* Jan–Feb: 35–37, 1998; Schwab et al., *Kidney Int.* 36: 707–711, 1989). However, these methods do not correlate well enough with blood flow rate and lack the sensitivity and specificity needed for accurate access surveillance.

At present, the most reliable methods for surveillance of access blood flow utilize conventional Doppler ultrasound (see Stauch et al., *Am. J. Kidney Dis.* 19: 554–557, 1992; Kirshbaum and Compton, *Am. J. Kidney Dis.* 25: 22–25, 1995; Findley et al., *Radiographics* 13: 983–999, 1993; Sands, *ASAIO J.* Jan–Feb: 41–43, 1998; Oates et al., *Ultrasound Med. Biol.* 16: 571–579, 1990; Sands et al., *ASAIO J.* 38: M524–M527, 1992) or indicator dilution techniques (see Depner, *ASAIO* Jan–Feb: 38–39, 1998; Krivitski, *Kidney Int.* 48: 244–250, 1995; Lindsay et al., *ASAIO J.* Jan–Feb: 62–67, 1998).

To evaluate a vascular access using Doppler ultrasound, an ultrasound unit with both imaging and spectral flow Doppler capabilities, termed duplex ultrasonography, is typically utilized. Access blood flow is calculated using the time-velocity integral of a spectrum obtained from a representative area of the access. The cross-sectional area of the access is measured via imaging, and from these measurements volume blood flow is calculated. However, Doppler ultrasound techniques are fraught with sources of operator error, most often associated with the determination of cross-sectional area. In addition, conventional Doppler ultrasound is labor intensive and expensive, such that measurements are not usually made with high enough frequency to effectively monitor the onset of reduced access flow.

Indicator dilution methods have also been utilized to measure access blood flow. U.S. Pat. No. 5,685,989 issued to Kravitski et al. discloses a dilution technique which uses ultrasonic sensors on the arterial and venous lines. For the measurement of access blood flow, the blood lines are reversed and a temporary recirculation is created. Then, a known quantity of an indicator, such as saline, is injected into the venous line. This dilutes the flow of blood in the access, resulting in Doppler velocity changes measured by the ultrasonic sensor on the arterial line. Because this change is proportional to the concentration of injected saline in the blood, access flow can be calculated. The use of other indicator dilution methods to determine blood flow can be found in U.S. Pat. No. 5,312,550 issued to Hester, U.S. Pat. No. 5,510,716 issued to Buffaloe, IV et al., and U.S. Pat. No. 5,644,240 issued to Brugger. Unfortunately, conditions affecting indicator mixing and recirculation of the indicator through the cardiovascular system can affect the accuracy of results using this method. Furthermore, due to the necessity for the reversal of blood lines during dialysis, dilution techniques are cumbersome and time-consuming.

DISCLOSURE OF THE INVENTION

Therefore, a principal object of the present invention is to provide a system and method for determining the blood flow rate in a vessel.

It is a further object of the present invention to provide a system and method for accurately measuring blood flow rate in a vessel without relying on a measurement of vessel cross-sectional area.

It is another object of the present invention to provide a system and method for determining blood flow rate in a hemodialysis access in a simple, safe, and efficient manner.

Accordingly, a system is provided for determining the blood flow rate in a vessel of a patient without requiring a measurement of the cross-sectional area of the vessel. A conduit is provided in communication with the vessel, and has an inlet for diverting blood from the vessel into the conduit. Disposed within the conduit is a pump for diverging blood out of the vessel using at least one pump flow rate. An ultrasonic sensor in communication with the vessel generates at least one Doppler frequency signal correlated with a blood flow rate in the vessel downstream from the inlet, wherein the downstream flow rate depends on the known pump flow rate and an unknown blood flow rate in the vessel upstream from the inlet. A processor is provided in communication with the ultrasonic sensor and the pump for determining the upstream flow rate from the signal and the pump flow rate.

Correspondingly, a method is provided for determining the blood flow rate in a vessel. The method includes diverting blood from the vessel at a diversion point to obtain a flow of diverted blood in a conduit, then pumping the diverted blood through the conduit using at least one pump flow rate. The method further comprises generating at least one Doppler frequency signal correlated with a blood flow rate in the vessel downstream from the diversion point, wherein the downstream flow rate depends on the known pump flow rate and an unknown blood flow rate in the vessel upstream from the diversion point. Lastly, the method includes processing the signal and the pump flow rate to obtain the upstream flow rate.

In one embodiment of the present invention, the vessel is a hemodialysis access, and the conduit comprises an external dialysis circuit. Alternatively, the conduit may comprise an intravascular catheter provided with either an intravascular or extravascular pump.

The above objects and other objects, features, and advantages of the present invention are more readily understood from a review of the attached drawings and the accompanying specification and claims.

BEST MODES FOR CARRYING OUT THE INVENTION

The present invention provides a system and method for determining the blood flow rate in a vessel, such as a hemodialysis access. Blood flow rate in the vessel is determined by diverting a portion of the blood from the vessel into a conduit, such as an external dialysis circuit, and applying the principle of conservation of mass. The conduit is configured to have a known blood flow rate created by a flow meter, such as a dialysis blood pump. The flow rate in the vessel downstream from the conduit is analyzed for at least one known flow rate generated in the conduit. The relationship between the downstream vessel flow and the known, conduit flow is then used to calculate the blood flow rate in the vessel upstream from the conduit, which represents the net vessel flow rate.

Figure 1:
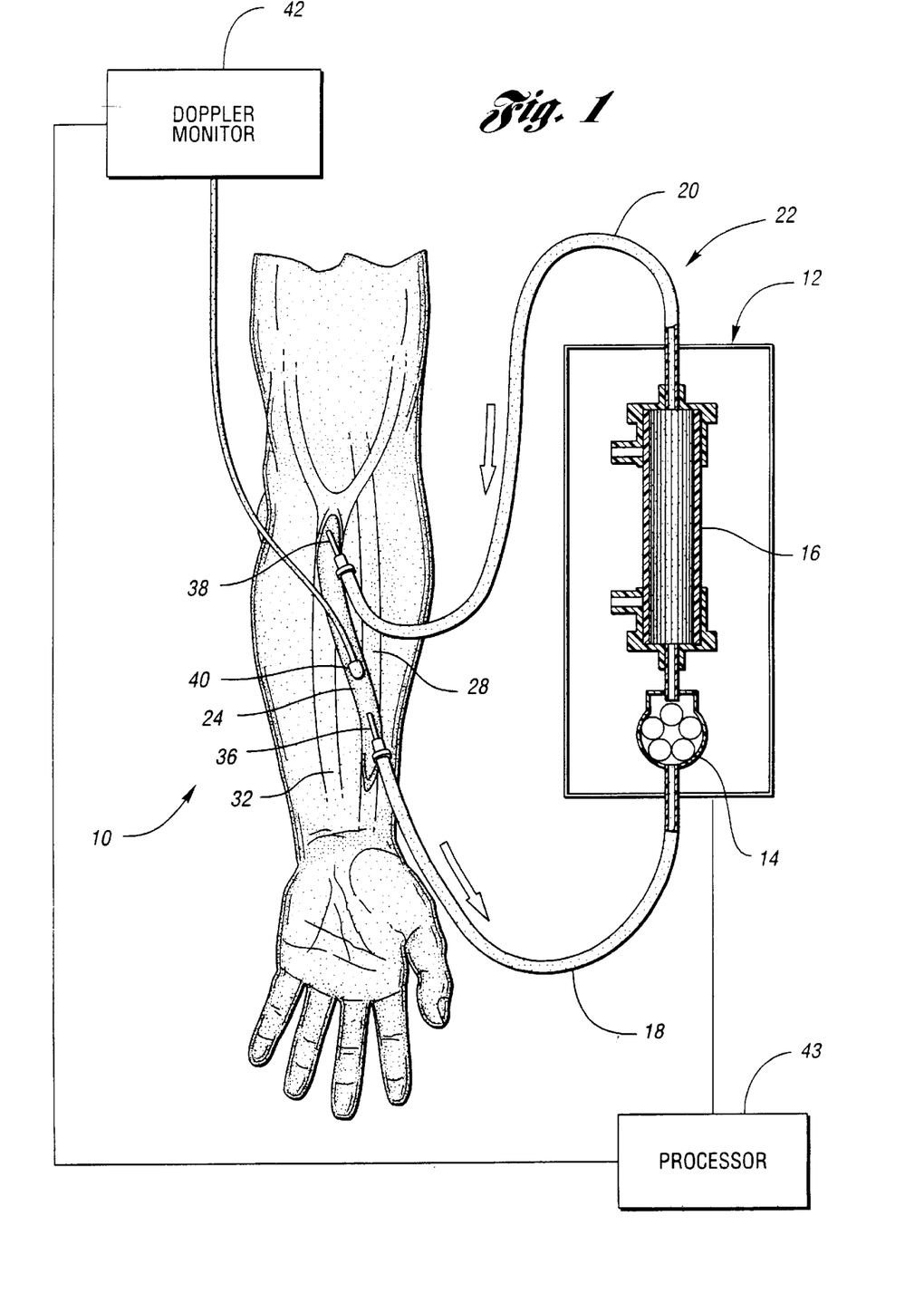
FIG. 1 illustrates a hemodialysis system in accordance with the present invention.
Figure 2:
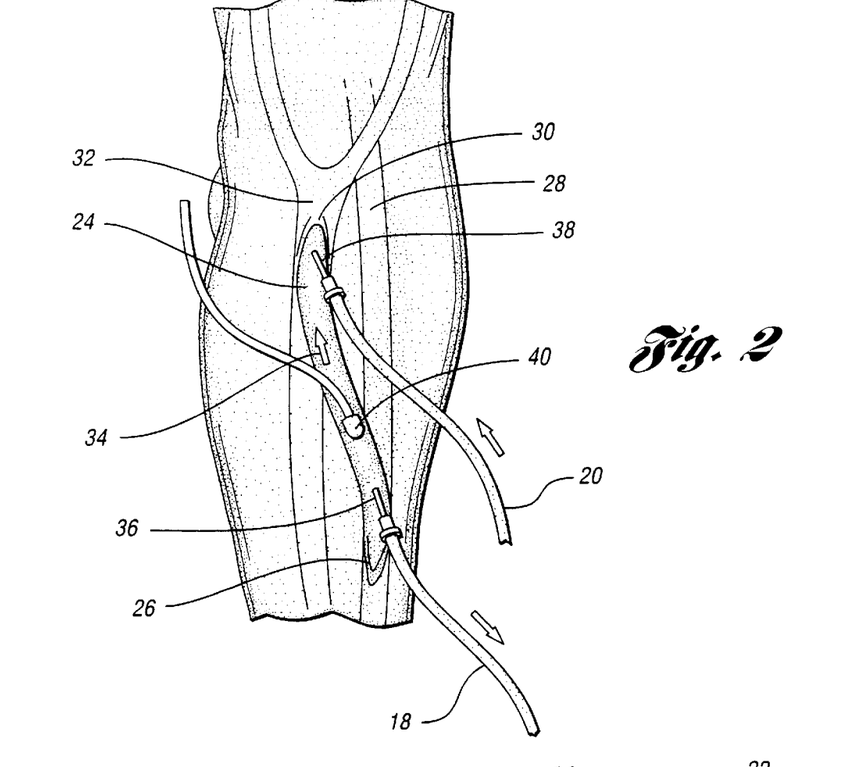
FIG. 2 is an enlarged view of the connections to a hemodialysis access within the system of FIG. 1.

In accordance with the present invention, a hemodialysis system is provided which is designated generally by reference numeral 10 in FIG. 1. Hemodialysis system 10 comprises conventional dialysis equipment 12, including a dialysis pump 14 and filter 16. Dialysis equipment 12 is provided on one end with an arterial line 18 and on the other end with a venous line 20, each constructed of sterile tubing. Arterial line 18, dialysis equipment 12, and venous line 20 form an external dialysis circuit, denoted by reference numeral 22. To perform hemodialysis, dialysis circuit 22 is connected to a patient's vessel 24, which is depicted in FIG. 1 as an arteriovenous shunt, or access. As best shown in FIG. 2, access 24 has a first end 26 connected to a patient's artery 28 and a second end 30 connected to a patient's vein 32. Access 24 may be an artificial subcutaneous vessel, such as a polytetrafluoroethylene (PTFE) graft, or a native fistula that is surgically created between artery 28 and vein 32. The normal direction of blood flow in access 24 is indicated by arrow 34.

Referring again to FIGS. 1 and 2, access 24 has two needles introduced into its lumen during dialysis, an arterial needle 36 connected to arterial line 18 and a venous needle 38 connected to venous line 20 for the return of blood to access 24. Blood is diverted into dialysis circuit 22 through arterial needle 36, flows through arterial line 18 to venous line 20 while being propelled by pump 14 at a known flow rate, and is returned to access 24 via venous needle 38. According to the invention, a first sensor 40 is provided in communication with access 24 to generate a signal correlated with the blood flow rate downstream from arterial needle 36 during dialysis. While first sensor 40 is preferably located downstream from arterial needle 36, more specifically between arterial needle 36 and venous needle 38, it is understood that first sensor 40 may be located anywhere suitable for detecting the downstream flow rate. Referring to hemodialysis system 10 depicted in FIG. 1, first sensor 40 would typically be secured to the skin of the patient's lower arm overlying access 24.

In a preferred embodiment, first sensor 40 comprises an ultrasonic sensor, and the signal generated by first sensor 40 comprises a Doppler ultrasound frequency signal relating the blood flow in access 24. Doppler ultrasound signal characteristics include peak velocity, signal amplitude, and time-averaged mean velocity, and each are related to blood flow rate and will vary according to blood flow rate. Of these characteristics, the most accurate correlate with blood flow rate is thought to be the time-averaged mean velocity, and this is the characteristic of the Doppler ultrasound signal which is preferably utilized in practicing the method of the present invention. However, it is understood that the present invention may utilize a measurement of any variable that relates predictably to volume flow rate, as will be explained below.

As shown in FIG. 1, first sensor 40 is connected to a signal monitor, preferably a Doppler monitor 42, and a processor 43 is provided in communication with the pump 14 and the Doppler monitor 42. For example, a suitable Doppler monitor would be Model 1052-C Vascular Mini-Lab manufactured by Parks Medical Electronics, Inc. (Aloha, Oreg.). In operation, first sensor 40 sends an ultrasound beam through the blood passing through access 24, and generates an output frequency signal proportional to the time-averaged mean Doppler velocity of the blood therein. While the present invention is described in the context of the ultrasound instrumentation described above, it is understood that the method of the present invention could be performed equally as well using other devices such as a magnetic resonance imaging (MRI) system, an electromagnetic blood flow meter, an intra-access pressure sensor, or other devices relating to flow measurement.

Figure 3:
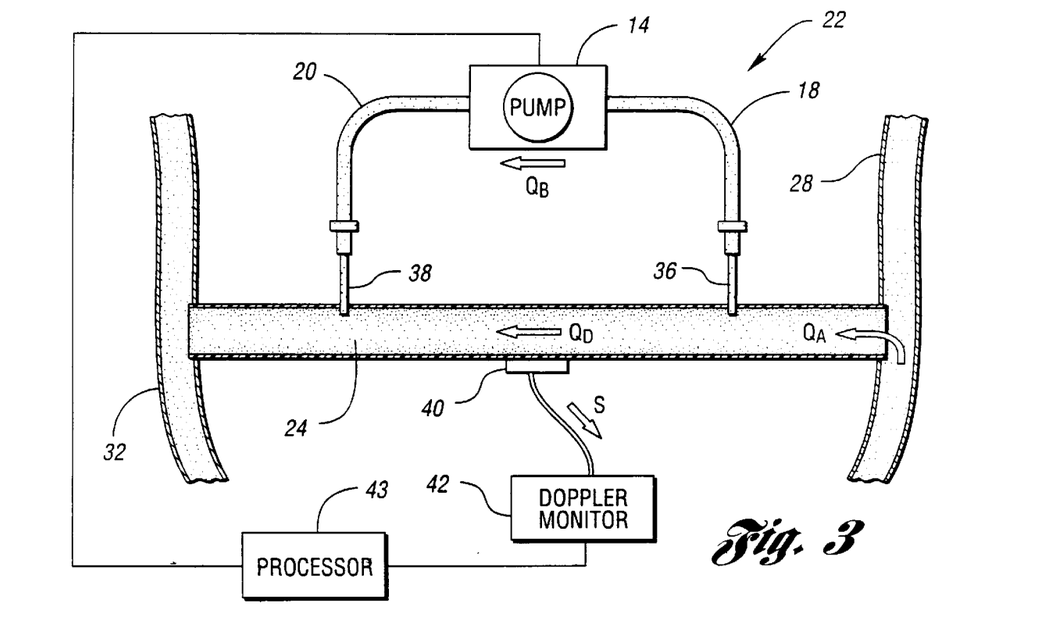
FIG. 3 is a schematic representation of the hemodialysis system of FIG. 1.

Access 24 has a blood flow rate dependent on numerous factors including systemic blood pressure, pre- and post-access geometry, and fluid viscosity. Referring now to the schematic diagram of FIG. 3, the access blood flow rate upstream from arterial needle 36 or downstream from venous needle 38 can be labeled $Q_A$. Access flow between arterial 36 and venous 38 needles will decrease during dialysis as a function of the blood diverted through dialysis circuit 22 at a known blood flow rate $Q_B$ controlled by pump 14. Assuming that the net flow through the system does not change during dialysis, the flow rate between needles 36 and 38 in access 24 during dialysis, denoted as $Q_D$, will follow the relationship $$Q_D + Q_B = Q_A \qquad (1)$$

or $$Q_D = Q_A - Q_B. \qquad (2)$$

In certain prior art methods, $Q_A$ is determined by measuring the velocity of blood flow in access 24 and multiplying this velocity by a measurement of the cross-sectional area of access 24. Because of the many factors involved in estimating an accurate access cross-sectional area and an accurate distribution of velocities thorough that area, the method of the present invention uses the relationship of equation (1) to independently derive the blood flow $Q_A$ as follows.

Figure 4:
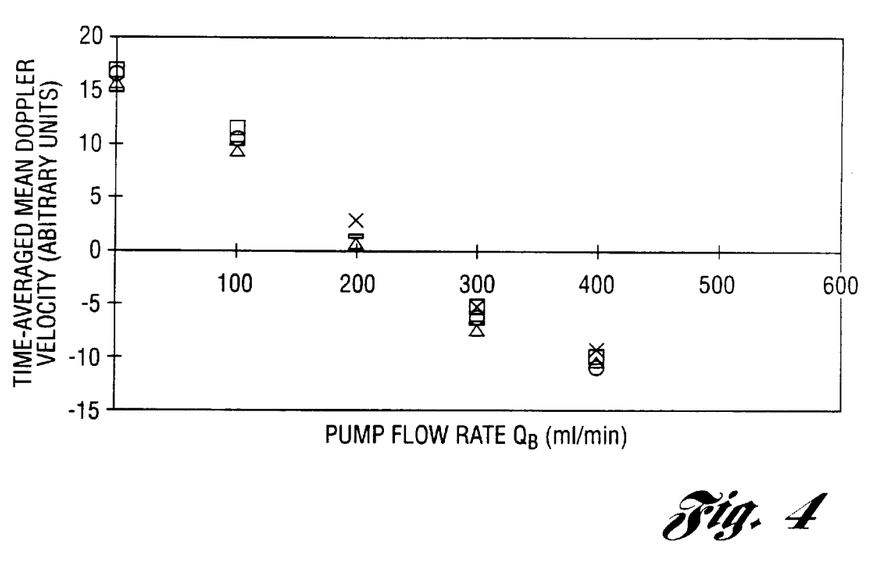
FIG. 4 is a graph depicting the linear relationship between the Doppler velocity signal and the dialysis pump flow rate.

First sensor 40 is located between arterial 36 and venous 38 needles as illustrated in FIG. 3, and the ultrasound signal generated by first sensor 40 is denoted as S. S is measured for at least two different values of $Q_B$ by varying the speed of dialysis pump 14. An example of the relationship between the signal S, in this case the time-averaged mean Doppler velocity, and the pump flow rate $Q_B$ is shown in the graph of FIG. 4. From these data, a modeling function is constructed for the signal S, where $S = f(Q_B)$. This modeling function may take the form of any one-to-one function, such as a linear, polynomial, or exponential function. As shown in FIG. 4, the time-averaged mean Doppler velocity signal has a tight, linear relationship to the flow $Q_B$, such that a linear regression function can be calculated.

Assuming a constant $Q_A$, $Q_D$ will decrease with increasing $Q_B$ such that the signal $S = f(Q_B)$ will decrease, as shown in FIG. 4. As $Q_D$ approaches zero, S will approach zero or a known value for S that corresponds to zero blood flow $Q_D$. This value for signal S is designated as $S_0$. The value for $S_0$ corresponds to the value for $Q_B = Q_A$ since $Q_D = 0$, as dictated by equations (1) and (2). Accordingly, $Q_B$ at the value $Q_A$ can be solved for graphically (the x-intercept) or by determining the inverse of the modeling function for S, namely $Q_B = f^{-1}(S)$. Then, setting $S = S_0$ yields the value for which $Q_B$ would equal $Q_A$, namely $Q_A = f^{-1}(S_0)$. Therefore, the modeled function derived from the signal S and knowledge of the blood flow rate $Q_B$ through dialysis circuit 22 allows determination of the flow rate $Q_A$ in access 24. It is understood that this method may be used to determine $Q_A$ regardless of whether $Q_A$ is less than, greater than, or equal to $Q_B$.

Although the method of the present invention has been described above as utilizing two measurements of the signal S to determine $Q_A$, only one measurement of S is required when the volume flow $Q_A$ through access 24 is less than the maximum blood flow rate $Q_B$ through dialysis circuit 22. This measurement value of S corresponds to the pump flow rate $Q_B$ where the downstream flow rate $Q_D$ is zero, such that $Q_B = Q_A$. Therefore, the speed of pump 14 may be increased to the value where the downstream signal S is zero in order to determine the value of $Q_A$ where $Q_A = Q_B$ with only one measurement.

Of particular note is the advantage that the system and method of the present invention do not require the magnitude of the cross-sectional area of access 24 to determine the flow $Q_A$. In fact, since the signal S is measured in arbitrary units, the absolute magnitude of the velocity of flow within access 24 is not necessary to accurately calculate access flow $Q_A$. As stated previously, the only requirement for the signal S is that it have a one-to-one relationship with $Q_B$, a requirement which is satisfied by the time-averaged mean Doppler velocity.

In addition to the access flow measurements determined by the system and method of the present invention, the periodic nature of the Doppler flow patterns through access 24 during the cardiac cycle may be observed as the speed of pump 14 is varied. In patients with lower access volume flow rates, periods of low, zero, and reversed Doppler velocity frequently occur during diastole as the speed of pump 14 is increased, even though forward flow is maintained during systole. This periodic forward and reverse flow during the cardiac cycle occurs as a result of increased flow into access 24 during systole which temporarily exceeds the flow diverted through dialysis circuit 22, followed rhythmically by comparatively low flow into access 24 during diastole which is exceeded by the pump flow rate resulting in reversed flow in the access during diastole alone. Using the system and method of the present invention, reversed diastolic flow in access 24, which can result in access recirculation, can be detected even though the net flow through access 24 is still forward as described below.

Since the blood flow rate $Q_A$ through access 24 varies with systole and diastole in the cardiac cycle, components of the signal S can give information to calculate other values of clinical interest. For example, instantaneous volume flow $Q_A$ in access 24 is higher during systole than diastole. The corresponding signal S will therefore show the same relationship since S is related to volume flow as described previously. For example, let $S_{min}$ represent the component of the signal S corresponding to a minimum flow rate $Q_{Amin}$ during diastole. $S_{min}$ can be measured at different values of $Q_B$ and a modeling function can be determined to calculate $Q_{Amin}$. As above, the minimum (diastolic) flow in access 24 may be determined using only one measurement as long as $Q_B$ equals or exceeds $Q_{Amin}$. In a similar fashion, systolic flow, the difference between systolic and diastolic flow, or other derived parameters may be determined by selecting a component or components of S and calculating a modeling function to determine the particular volume flow. In this way, the instantaneous volume flow throughout the cardiac cycle can be determined.

A special case exists when the access blood flow $Q_A$ varies with the flow $Q_B$ for different speeds of dialysis pump 14. As blood is diverted through dialysis circuit 22, pressure within access 24 may fall and $Q_A$ may therefore increase as pump flow rate $Q_B$ increases. The present invention provides the following system and method which correct for any dependence of $Q_A$ on $Q_B$, assuming that the signal S varies substantially linearly with volume flow, as is the case with time-averaged mean Doppler velocity. As above, the blood flow between arterial 36 and venous 38 needles is defined as $Q_D = Q_A - Q_B$. $Q_A(Q_B)$ designates the function $Q_A$ for each pump flow rate $Q_B$, since $Q_A$ is postulated to change with each change in $Q_B$.

Figure 5:
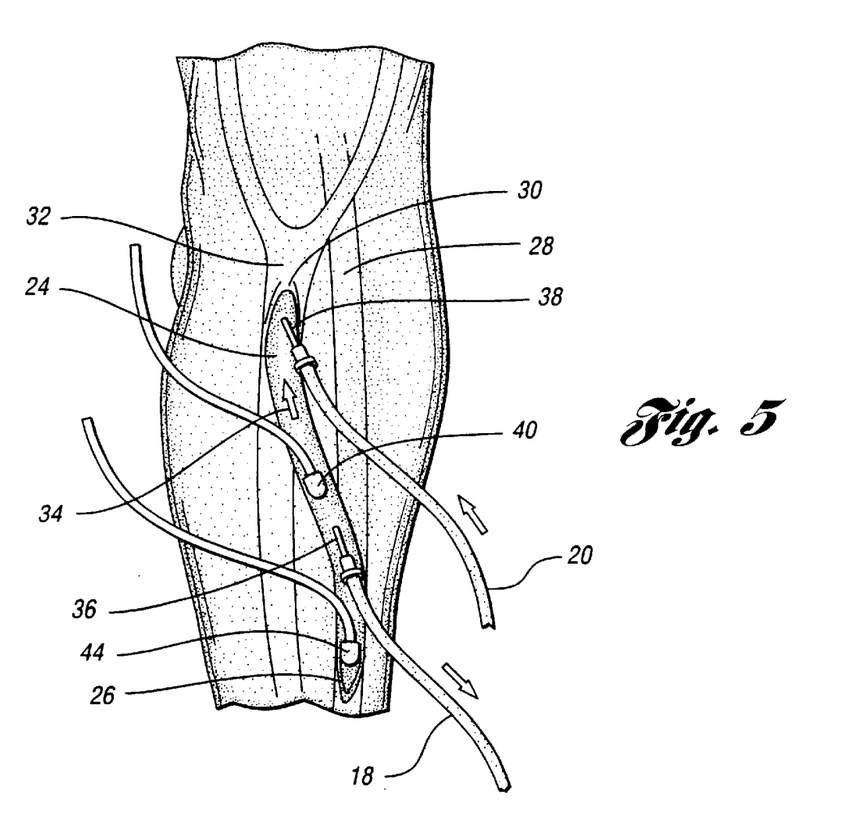
FIG. 5 depicts an alternative monitoring configuration of the hemodialysis access within the system of FIG. 1.
Figure 6:
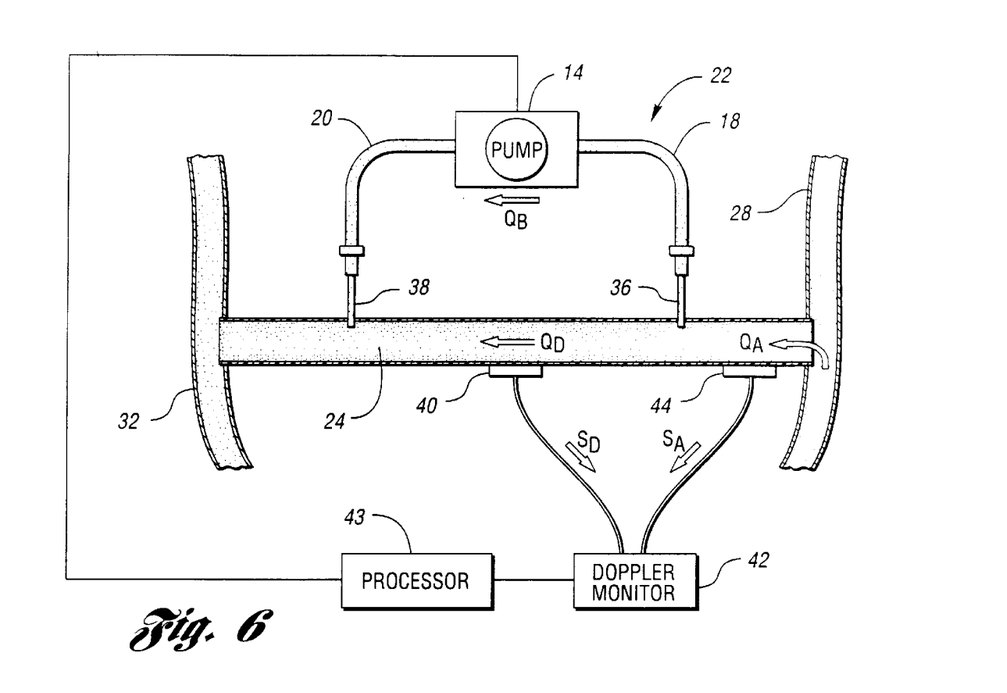
FIG. 6 is a schematic representation of a hemodialysis system configured as in FIG. 5.

Referring now to FIGS. 5 and 6, $S_D$ is defined to be the signal provided by first sensor 40 located between arterial 36 and venous 38 needles corresponding to the flow $Q_D$. In this embodiment of the invention, a second sensor 44, preferably located upstream from arterial needle 36, provides a signal $S_A$ corresponding to access flow $Q_A$. These signals are assumed to vary with $Q_B$, giving $S_D(Q_B)$ and $S_A(Q_B)$ for each pump flow rate $Q_B$.

Given this dependence on $Q_B$, $S_D$ and $S_A$ correspond to the same blood flow rate when $Q_B=0$. Therefore, $S_A$ can be multiplied by a constant to give $S_A'$ that will equal $S_D$ when $Q_B=0$, or $$S_A'(0) = C^* S_A(0) = S_D(0) \quad (3)$$

where $C = S_D(0)/S_A(0)$. Accordingly, the signal $S_A'$ will correspond to the increase in $Q_A$ with increasing $Q_B$. Referring to equation (2), $Q_D$ will fall with increasing $Q_B$ by the amount $Q_B$ less the increase in inflow $Q_A(Q_B) - Q_A(0)$. Subtracting the corresponding change in signal $S_A'(Q_B) - S_A'(0)$ from $S_D$ gives a correction allowing one to solve for $Q_A$.

In an alternative embodiment of the present invention, external dialysis circuit 22 is not a required component of the system for measuring the blood flow rate in vessel 24. In the embodiments shown in FIGS. 7–9, an intravascular catheter 46 provided with either an extravascular or intravascular pump is placed in vessel 24. The blood flow through any vessel 24 can be measured with catheter 46 using the same equations and relationships described previously. For instance, catheter 46 could be placed in the pulmonary artery to measure cardiac output, or in the superior or inferior vena cavae to measure venous return. Alternatively, catheter 46 could be combined with a left or right ventricular assist device to monitor the function thereof.

Figure 7:
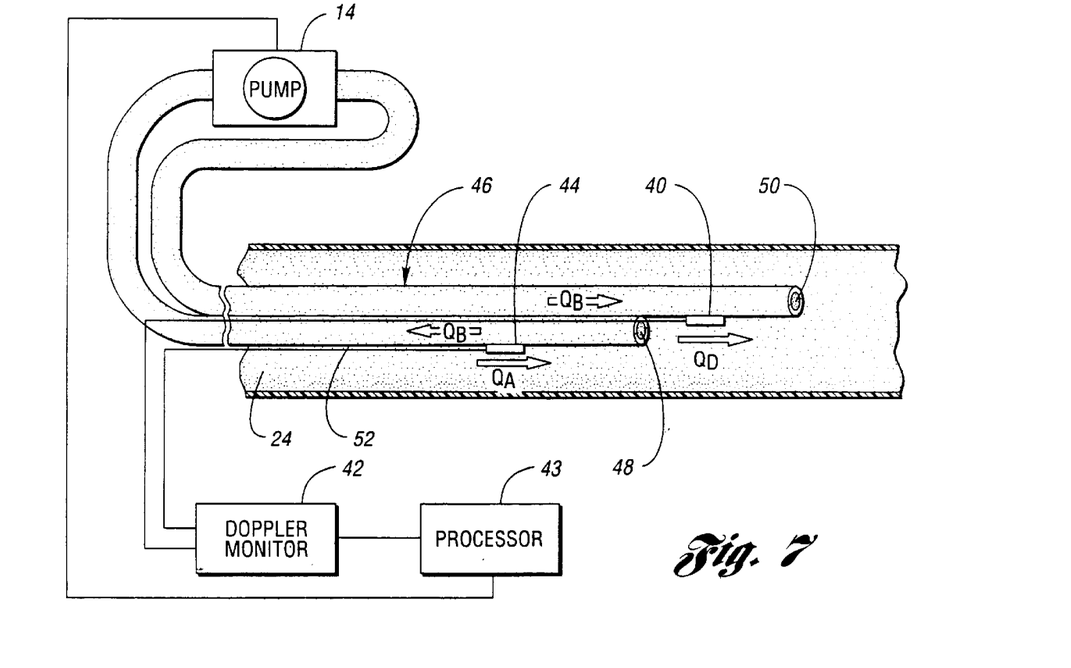
FIG. 7 shows a first embodiment of a blood flow rate measuring system in accordance with the present invention.

In the embodiment shown in FIG. 7, catheter 46 is depicted as a conventional dual lumen catheter having an inlet 48 which allows blood to be diverted from vessel 24 and into catheter 46. Blood travels through catheter 46 at a known flow rate $Q_B$ generated by an extravascular pump (not shown) similar to dialysis pump 14, and is returned to vessel 24 thorough an outlet 50. However, it should be understood that the return of blood to vessel 24 via outlet 50 is not required to carry out the method of the present invention. First sensor 40 is preferably affixed to an outside surface 52 of catheter 46 downstream from inlet port 48, more specifically between inlet 48 and outlet 50, to generate the signal $S_D$ corresponding to the flow $Q_D$ as it varies with different pump flow rates $Q_B$. Optionally, second sensor 44 may be affixed to outside catheter surface 52 upstream from inlet port 48 to provide a measure of $Q_A$ and any dependence thereof on $Q_B$. Of course, sensors 40 and 44 may be located anywhere suitable for detecting flows $Q_D$ and $Q_A$, respectively.

Figure 8:
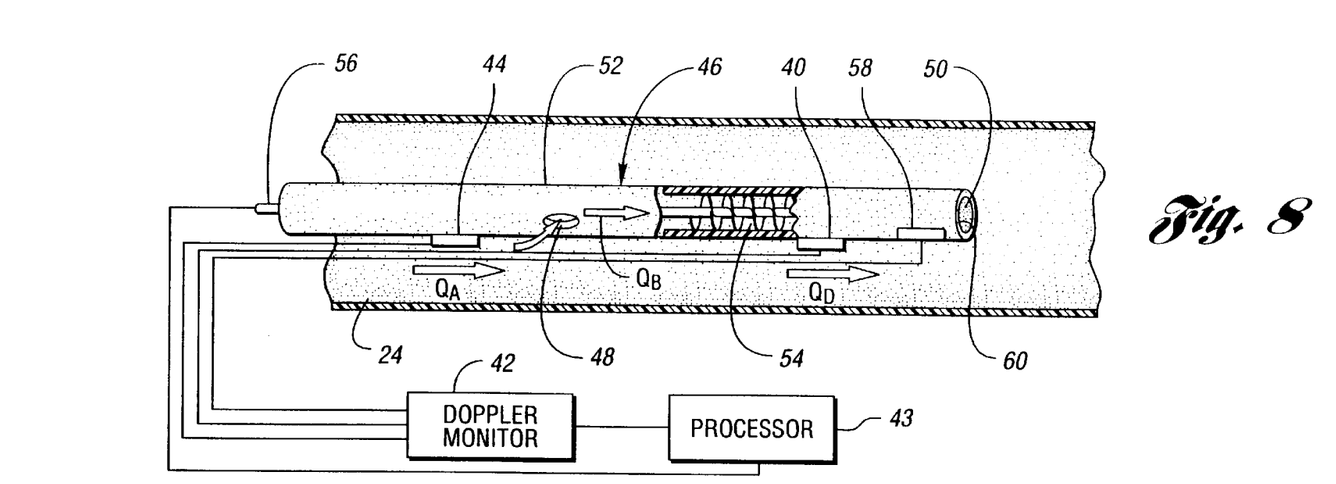
FIG. 8 shows a second embodiment of the blood flow rate measuring system of FIG. 7 which utilizes an intravascular pump.
Figure 9:
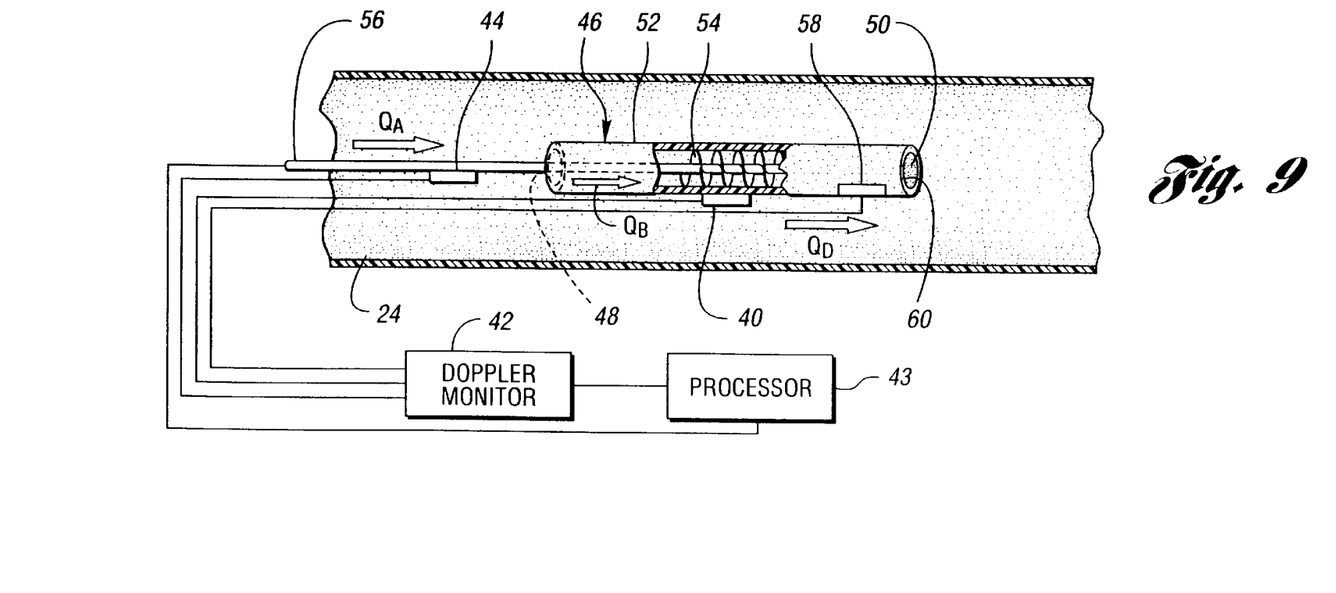
FIG. 9 shows an alternative configuration of the blood flow rate measuring system of FIG. 8.

In the embodiment depicted in FIG. 8, catheter 46 is shown as a single lumen catheter which incorporates an intravascular pump 54 to generate $Q_B$. Pump 54 may be of a screw, peristaltic, occluding, or any other type. Pump 54 is driven by a drive line 56 which extends through catheter 46 and is connected to an external motor (not shown). In addition to first 40 and second 44 sensors, a third sensor 58 may optionally be affixed to an inside surface 60 of catheter 46 to provide an independent measure of $Q_B$. In an alternative embodiment shown in FIG. 9, catheter 46 is constructed as a cylindrical housing which does not extend extravascularly, and optional second sensor 44 is affixed to drive line 56.

It is understood, of course, that while the form of the invention herein shown and described constitutes a preferred embodiment of the invention, it is not intended to illustrate all possible forms thereof. For example, the system and method of the present invention may be practiced using body fluids other than blood. Furthermore, the invention may be utilized for purposes ancillary to the measurement of blood flow rate in a vessel, such as use as an in vivo flow phantom for testing the accuracy of devices that measure volume flow. It will be understood that the words used are words of description rather than limitation, and that various changes may be made without departing from the spirit and scope of the invention disclosed.

What is claimed is:

1. A system for determining flow rate of blood in a vessel which communicates the blood between two locations of a patient, the system comprising:
    a conduit in communication with the blood in the vessel, the conduit having a diversion point for diverting the blood from the vessel into the conduit, wherein the vessel has a flow rate ($Q_A$) upstream from the diversion point and a flow rate ($Q_D$) downstream from the diversion point;
    a pump connected to the conduit for pumping the diverted blood in the conduit using a pump flow rate;
    an ultrasonic sensor in communication with the blood in the vessel downstream from the diversion point, the ultrasonic sensor sensing the downstream flow rate ($Q_D$) and generating at least two downstream Doppler frequency signals including a first downstream Doppler frequency signal when the pump has a first pump flow rate and a second downstream Doppler frequency signal when the pump has a second pump flow rate; and
    a processor connected to the ultrasonic sensor and the pump, the processor determining the upstream flow rate ($Q_A$) when the pump has a selected pump flow rate from the first and second downstream Doppler frequency signals and the selected pump flow rate.

2. The system of claim 1, wherein the vessel is a hemodialysis access.

3. The system of claim 1, wherein the conduit further comprises means for returning the diverted blood from the conduit into the vessel.

4. The system of claim 3, wherein the conduit comprises an external dialysis circuit.

5. The system of claim 1, wherein the conduit comprises an intravascular catheter.

6. The system of claim 1, wherein the processor determines a time-averaged mean Doppler velocity from at least one of the first and second downstream Doppler frequency signals.

7. The system of claim 1, wherein the vessel comprises native tissue.

8. The system of claim 1, wherein the vessel comprises synthetic material.

9. The system of claim 1, further comprising a second ultrasonic sensor connected to the processor and in communication with the blood in the vessel upstream from the diversion point, the second ultrasonic sensor sensing the upstream flow rate ($Q_A$) and generating at least tow upstream Doppler frequency signals including a first upstream Doppler frequency signal when the pump has the first pump flow rate and a second upstream Doppler frequency signal when the pump has the second pump flow rate, and the processor determining a correction in the upstream flow rate ($Q_A$) from the first and second upstream Doppler frequency signals, the first and second downstream Doppler frequency signals, and the selected pump flow rate.

10. A system for determining flow rate of blood in a hemodialysis access which communicates the blood between two locations of a patient, the system comprising:

an external dialysis circuit in communication with the blood in the access, the circuit comprising an inlet for diverting the blood from the access into the circuit, and an outlet for returning the blood from the circuit into the access, wherein the access has a flow rate ($Q_D$) downstream from the inlet and before the outlet, and a flow rate ($Q_A$) upstream from the inlet;

a pump disposed between the inlet and the outlet, the pump pumping the diverted blood in the circuit and returning the diverted blood into the access using a pump flow rate;

an ultrasonic sensor in communication with the blood in the access downstream from the inlet and before the outlet, the ultrasonic sensor sensing the downstream flow rate ($Q_D$) and generating at least two downstream Doppler frequency signals including a first downstream Doppler frequency signal when the pump has a first pump flow rate and a second downstream Doppler frequency signal when the pump has a second pump flow rate; and a processor connected to the ultrasonic sensor and the pump, the processor determining the upstream flow rate ($Q_A$) when the pump has a selected pump flow rate first and second downstream Doppler frequency signals and the selected pump flow rate.

11. The system of claim 10, wherein the processor determines a time-averaged mean Doppler velocity from at least one of the first and second downstream Doppler frequency signals.

12. The system of claim 10, wherein the access comprises native tissue.

13. The system of claim 10, wherein the access comprises synthetic material.

14. The system of claim 10, further comprising a second ultrasonic sensor connected to the processor and in communication with the blood in the access upstream from the diversion point, the second ultrasonic sensor sensing the upstream flow rate ($Q_A$) and generating at least two upstream Doppler frequency signals including a first upstream Doppler frequency signal when the pump has the first pump flow rate and a second upstream Doppler frequency signal when the pump has the second pump flow rate, and the processor determining a correction in the upstream flow rate ($Q_A$) from the first and second upstream Doppler frequency signals, the first and second downstream Doppler frequency signals, and the selected pump flow rate.

15. A system for determining flow rate of blood in a vessel which communicates the blood between two locations of a patient, the system comprising:

an intravascular catheter in communication with the blood in the vessel, the catheter having an inlet for diverting the blood from the vessel into the catheter and an outlet for returning the blood from the catheter into the vessel, wherein the vessel has a flow rate ($Q_D$) downstream from the inlet and before the outlet, and a flow rate ($Q_A$) upstream from the inlet;

a pump connected to the catheter, the pump pumping the diverted blood in the catheter and returning the blood into the vessel using a pump flow rate;

an ultrasonic sensor in communication with the blood in the vessel downstream from the inlet and before the outlet, the ultrasonic sensor sensing the downstream flow rate ($Q_D$) and generating at least two downstream Doppler frequency signals including a first downstream Doppler frequency signal when the pump has a first pump flow rate and a second downstream Doppler frequency signal when the pump has a second pump flow rate; and a processor connected to the ultrasonic sensor and the pump, the processor determining the upstream flow rate ($Q_A$) when the pump has a selected pump flow rate from the first and second downstream Doppler frequency signals and the selected pump flow rate.

16. The system of claim 15, wherein the pump is positioned outside the vessel.

17. The system of claim 16, wherein the pump is positioned inside the vessel.

18. The system of claim 15, wherein the processor determines a time-averaged mean Doppler velocity from at least one of the first and second downstream Doppler frequency signals.

19. The system of claim 15, wherein the vessel comprises native tissue.

20. The system of claim 15, wherein the vessel comprises synthetic material.

21. The system of claim 15, further comprising a second ultrasonic sensor connected to the processor and in communication with the blood in the vessel upstream from the inlet, the second ultrasonic sensor sensing the upstream flow rate ($Q_A$) and generating at least two upstream Doppler frequency signals including a first upstream Doppler frequency signal when the pump has the first pump flow rate and a second upstream Doppler frequency signal when the pump has the second pump flow rate, and the processor determining a correction in the upstream flow rate ($Q_A$) from the first and second upstream Doppler frequency signals, the first and second downstream Doppler frequency signals, and the selected pump flow rate.

22. A method for determining flow rate of blood in a vessel which communicates the blood between two locations of a patient, the method comprising:

providing a conduit in communication with the blood in the vessel, the conduit having a diversion point;

diverting the blood from the vessel at the diversion point of the conduit, wherein the vessel has a flow rate ($Q_A$) upstream from the diversion point and a flow rate ($Q_D$) downstream from the diversion point;

pumping the diverted blood into the conduit at a pump flow rate;

sensing the downstream flow rate ($Q_D$) and generating at least two downstream Doppler frequency signals including a first downstream Doppler frequency signal when pumping the diverted blood into the conduit at a first pump flow rate and a second downstream Doppler frequency signal when pumping the diverted blood into the conduit at a second pump flow rate;

selecting a selected pump flow rate; and processing the first and second downstream Doppler frequency signals and the selected pump flow rate to determine the upstream flow rate ($Q_A$).

23. The method of claim 22, further comprising returning the diverted blood into the vessel at a return point of the conduit.

24. The method of claim 22, wherein the processing step further comprises determining a time-averaged mean Doppler velocity from at least one of the first and second downstream Doppler frequency signals.

25. The method of claim 22, further comprising sensing the upstream flow rate ($Q_A$) and generating at least two upstream Doppler frequency signals including a first upstream Doppler frequency signal when pumping the diverted blood into the conduit at the first pump flow rate and a second upstream Doppler frequency signal when pumping the diverted blood into the conduit at the second pump flow rate, and determining a correction in the upstream flow rate ($Q_A$) from the first and second upstream Doppler frequency signals, the first and second downstream Doppler frequency signals, and the selected pump flow rate.

* * * * *